United States Patent [19]

Chan et al.

[11] Patent Number: 5,652,097
[45] Date of Patent: Jul. 29, 1997

[54] IN VITRO TEST TO EVALUATE THE INHIBITION POTENCY OF ANGIOTENSIN II ANTAGONISTS ON ANGIOTENSINOGEN

[75] Inventors: John S. D. Chan, Ville LaSalle; Serge Carrière, Vaudreuil-sur-le-lac, both of Canada

[73] Assignee: Universite de Montreal, Montreal, Canada

[21] Appl. No.: 355,626

[22] Filed: Dec. 14, 1994

[51] Int. Cl.⁶ .................................................. C12Q 1/68
[52] U.S. Cl. .................................... 435/6; 435/370
[58] Field of Search ................... 435/6, 240.2, 172.3

[56] References Cited

U.S. PATENT DOCUMENTS 5,112,757  5/1992  Guguen-Guillouzo et al. ..... 435/240.2

OTHER PUBLICATIONS

Sambrook et al., *Molecular Cloning: A Laboratory Manual*, 2nd ed., 1989, *CSU Laboratory* Press, p. 16.3–16–4,16.17–16.22,16.30–16.40.

Singleton et al., *Dictionary of Microbiolgy and Molecular Biology*, 2nd ed., 1987, Wiley and Sons, New York, pp. 889, 890, 902–904.

Fukamizu et al., *J. Biol. Chem.*, vol. 13, 1990, pp. 7576–7582.

Zhao et al., *Cell. Mol. Biol.*, vol. 38, 1992, pp. 71–80.

Klett et al., *Endocrinology*, vol. 130, 1992, pp. 3660–3668.

U.S. application No. 07/234,368 Cole et al., filed Dec. 14, 1988.

Chan JSD et al., *Pediatr. Nephrol.*, 1990, 4:429–435.

Wang TT et al., *Kidney Int.*, 1994, 46:703–710.

Ming M et al., *Am. J. Hypertens.*, 1993, 6:141–148.

*Primary Examiner*—James S. Ketter
*Attorney, Agent, or Firm*—Klauber & Jackson

[57] ABSTRACT

The present invention relates to an in vitro test by recombinant DNA technology for the evaluation of the potency of various angiotensin II (AII) antagonists on the inhibition of expression of angiotensinogen (ANG) gene in vivo. A transformed human liver cell line capable of expressing human angiotensinogen-growth hormone, which includes at least one DNA construct coding for at least a 5'-flanking region of the ANG operatively linked upstream to human growth hormone gene. An in vitro test for the evaluation of the potency of various angiotensin II (AII) antagonists on the inhibition of expression of angiotensinogen (ANG) gene in vivo, which comprises administering AII antagonists to a transformed human liver cell line of claim 1 and monitoring the expression of human angiotensinogen-growth hormone.

6 Claims, 7 Drawing Sheets

IN VITRO TEST TO EVALUATE THE INHIBITION POTENCY OF ANGIOTENSIN II ANTAGONISTS ON ANGIOTENSINOGEN

BACKGROUND OF THE INVENTION (a) Field of the Invention

The invention relates to an in vitro test by recombinant DNA technology to be able to evaluate the potency of various angiotensin II (AII) antagonists on the inhibition of expression of angiotensinogen (ANG) gene in vivo.

(b) Description of Prior Art

Angiotensin II (AII) is derived from the precursor glycoprotein, angiotensinogen (ANG) which is synthesized predominantly in the liver via successive cleavage by renin and angiotensin-converting enzyme (ACE). The evidence for a direct relationship between renin-angiotensin-system (RAS) and the development of hypertension was reported and it was demonstrated that transgenic mice which carry an exogenous angiotensinogen (ANG) gene and/or renin gene and express high levels of plasma angiotensinogen and Angiotensin II will develop high blood pressure. These studies demonstrated unequivocally that angiotensinogen is an important component for the development of high blood pressure but the expression of renin and angiotensin-converting enzyme is also equally important.

The expression of the angiotensinogen gene in mouse hepatoma (Hepa 1–6) cells was previously reported and shown that dexamethasone (DEX) stimulates the expression of fusion genes containing the 5'-flanking region of the rat angiotensinogen (ANG) gene fused with a bacterial chloramphenicol acetyl transferase (CAT) coding sequence as reporter, pOCAT (ANG N-1498/+18), in a dose-dependent manner (Ming M. et al., *Am. J. Hypertens.*, 1993, 6:141–148). Furthermore, it was demonstrated that the addition of 8-Bromo-cAMP (8-Br-cAMP) enhanced the stimulatory effect of dexmethasone (DEX) on the expression of ANG-CAT fusion genes (Ming M. et al., *Am. J. Hypertens.*, 1993, 6:141–148). The addition of 8-Br-cAMP alone, however, had no stimulatory effect on the expression of the ANG-CAT fusion genes. These studies suggest that DEX and cAMP might act synergistically or co-operatively to stimulate the expression of the ANG gene in the liver.

Angiotensin II (AII) is known to stimulate the synthesis and secretion of ANG in vivo and in vitro. The stimulatory effect of angiotensin II is apparently mediated via the angiotensin II-receptors ($AT_1$-receptors).

It would be highly desirable to be provided with means to determine if the addition of angiotensin II-receptors ($AT_1$- and AT2-receptors) antagonists could inhibit the stimulatory effect of angiotensin II on the expression of ANG gene.

There is disclosed in U.S. Pat. No. 5,112,757 issued in the name of Guguen-Guillouzo et al. on May 12, 1992, a method for culturing human hepatocytes so that they maintain hepatocyte functions at a high level for an extended period of time.

There is disclosed in U.S. patent application No. 07/284, 368 filed on Dec. 14, 1988 in the name of Cole et al., a human liver epithelial cell line with extended life spans which more reliably predict the affect of various chemical assaults on the cell in carcinogen and mutagen research, metabolism research and other applications for cell lines.

None of these documents provides a culture of human hepatocytes which could be used to determine if the addition of angiotensin II-receptors ($AT_1$- and $AT_2$-receptors) antagonists could inhibit the stimulatory effect of angiotensin II on the expression of ANG gene.

SUMMARY OF THE INVENTION

One aim of the present invention is to provide an in vitro test by recombinant DNA technology to be able to evaluate the potency of various angiotensin II (AII) antagonists on the inhibition of expression of angiotensinogen (ANG) gene in vivo.

Another aim of the present invention is to provide means to determine if the addition of angiotensin II-receptors ($AT_1$- and $AT_2$-receptors) antagonists could inhibit the stimulatory effect of angiotensin II on the expression of ANG gene.

Another aim of the present invention is to provide a liver cell line, transformed or transfected with the angiotensinogen gene, for the evaluation of potency of angiotensin II antagonists on the inhibition of angiotensinogen gene in vitro.

In accordance with the present invention, there is demonstrated that the addition of angiotensin II-receptors ($AT_1$- and $AT_2$-receptors) antagonists could inhibit the stimulatory effect of angiotensin II on the expression of ANG-GH or ANG-CAT fusion genes (pOGH (ANG N-1498/+18) or pOCAT (ANG N-1498/+18)) in human (Hep G-2) hepatoma cells. More specifically, there is demonstrated the evidence that Lorsatan™, Saralasin™ and Staurosporine™ inhibit the stimulatory effect of angiotensin II on ANG gene expression, demonstrating that the stimulatory effect of angiotensin II is mediated via the $AT_1$-receptor and the protein kinase C pathway.

In accordance with the present invention there is provided a transformed human liver cell line capable of expressing human angiotensinogen-growth hormone, which comprises at least one DNA construct coding for at least a 5'-flanking region of the ANG operatively linked upstream to human growth hormone gene.

In accordance with the present invention the transformed human liver cell line consists of a DNA construct selected from the group consisting of ANG-GH, ANG-CAT, pOCAT and pOGH fusion genes. The preferred transformed human liver cell line of the present invention includes a pOGH DNA construct and has an ATCC deposit number CRL-11763.

In accordance with the present invention there is also provided an in vitro test for the evaluation of the potency of various angiotensin II (AII) antagonists on the inhibition of expression of angiotensinogen (ANG) gene in vivo, which comprises administering AII antagonists to a transformed human liver cell line of the present invention and monitoring the expression of human angiotensinogen-growth hormone.

The preferred in vitro test of the present invention consists of an administration which is effected using a concentration of about $10^{-9}$ to about $10^{-5}$ mol/L of antagonist. The preferred in vitro test of the present invention consists of a radioimmunoassay which is effected using immunoreactive human growth hormone (IR-hGH).

DETAILED DESCRIPTION OF THE INVENTION

In accordance with the present invention, a plasmid (fusion gene) containing the 5'-flanking DNA sequence of the ANG gene (the DNA fragment which mainly controls the transcription of the ANG gene) fused with the human growth hormone (hGH) gene as reporter, pOGH (ANG N-1498/+18), has been constructed. This fusion gene is stably transfected in human (Hep G-2) hepatoma cells. The transformants which express the immunoreactive-hGH (IR-hGH) and are resistant to the addition of the aminoglycoside G418 (G418 is toxic to cells which do not express the neomycine gene) will be selected.

The selected transformants will be used for in vitro assay and will be able to monitor the potency of various AII antagonists on the inhibition of expression of the angiotensinogen-growth hormone (ANG-GH) fusion gene.

Materials

Restriction and modifying enzymes were purchased either from Bethesda Research Laboratories (BRL, Burlington, Ontario, Canada), Boehringer-Mannheim (Dorval, Quebec, Canada) or Pharmacia Inc. (Baie d'Urfe, Quebec, Canada).

The plasmid, pRSV-Neo, containing the coding sequence for neomycin (Neo) with the Rous Sarcoma Virus (RSV) enhancer/promoter sequence fused in the 5'-end of the neomycin gene was a gift from Dr. Teresa Wang (Dept. of Pathology, Stanford University, Stanford, Calif., U.S.A.).

The expression vector pRSVCAT containing the coding sequence for chloramphenicol acetyl transferase (CAT) with Rous Sarcoma Virus enhancer/promoter sequence fused to the 5'-end of the CAT coding sequence, respectively, was a gift from Dr. Joel F. Habener (Lab. of Molec. Endocrinol., Massachusetts General Hospital, Boston, USA). Human $AT_1$-receptor cDNA was cloned in our laboratory from a human liver cDNA library (purchased from Strategene Cloning Systems, La Jolla, Calif., USA), by employing a 60-mers oligonucleotide probe corresponding to the published coding nucleotide sequence of human $AT_1$-receptor (N+1 to+N 60). The cloned $hAT_1$-receptor cDNA was subcloned in plasmid Bluescript, tentatively named $pJC-hAT_1$. The cloned $hAT_1$-receptor cDNA has an apparent molecular weight of 2.0 kilobase-pairs, as analyzed in 0.8% Agarose gel with a coding sequence identical to human $AT_1$-receptor cDNA.

Human ANG cDNA was also cloned in our laboratory from the same human liver cDNA library (purchased from Strategene Cloning Systems, La Jolla, Calif., USA), by employing a 60-mers oligonucleotide probe corresponding to the published coding nucleotide sequence of human ANG (N-30 to N+30). The cloned ANG cDNA was amplified by polymerase chain reaction (DNA Thermal Cycler™, Perkin, Elmer Cetus, Norwalk, Conn., U.S.A.), by employing primers corresponding to the coding region of the hANG, nucleotides N+1 to N+30 (Primer 1) and nucleotides N+1333 to N+1364 (Primer 2). The amplified hANG cDNA was subsequently subcloned in the plasmid Bluescript, tentatively named pJC-hANG. The cloned hANG cDNA has the same sequence as human angiotensinogen.

All oligonucleotides were synthesized in our laboratory using model 391 DNA synthesizer™ (Applied Biosystems Inc., Foster City, Calif., U.S.A.).

Alpha-[35S]dATP (>1000 Ci/mmol), alpha-[32P]CTP (800 Ci/mmol), gamma-[32P]ATP (3000 Ci/mmol), D-Threo-[1,2$^{14}$C]-chloramphenicol and Na-$^{125}$I were purchased from New England Nuclear, Dupont (Boston, Mass, USA).

Human AII and Saralasin™ were purchased from Sigma Chemical (St-Louis, Mo., USA). The Staurosporine™ and CGP-42112A# were purchased from Research BioChemicals Inc. (RBI, Natick, Mass., USA). Lorsatan# (or Dup 753) was a gift from Dr. Donald D. Smith (Dupont Merck Pharmaceutical Co., Wilmington, Del., USA).

Thin layer chromatography plates were purchased from Fisher Scientific Ltd. (Montréal, Québec, Canada). Other reagents were molecular biology grade and obtained from Sigma Chemicals, Bethesda Research Laboratories (BRL, Burlington, Ontario, Canada) or Pharmacia Inc. (Baie d'Urfe, Quebec, Canada).

Construction of Fusion Genes

The method of construction of pOGH (ANG N-1498/+18) has been described previously (Chan JSD et al., Pediatr. Nephrol., 1990, 4:429–435). The sequences and orientation for all fusion genes and the cloned $hAT_1$-receptor cDNA and hANG cDNA were confirmed by dideoxy sequencing and restriction enzyme digestion mapping.

Cell Culture

The human hepatoma (Hep G-2) cell lines were obtained from the American Type Culture Collection (Rockville, Md.). The Hep G-2 cells were grown in 100×20 mm plastic Petri dishes (Gibco, Burlington, Ontario, Canada) using Dulbecco's Modified Eagle's Medium (DMEM), pH 7.20, supplemented with 10% fetal bovine serum (FBS), 50 units/ ml of penicillin and 50 µg/ml of streptomycin. The cells were incubated in a humidified atmosphere of 95% $O_2$, 5% $CO_2$ at 37° C. For subculturing, cells were trypsinized (0.05% trypsin and EDTA) and plated at $3.5×10^4$ cells/cm$^2$.

Northern Blot Analysis

Total cellular RNA was prepared from Hep G-2 cells and Hep G-TW7 by guanidium isothiocyanate/cesium chloride gradient as previously described (Ming M. et al., Am. J. Hypertens., 1993, 6:141–148). Thirty (30) µg of total RNA was processed with electrophoresis through a 1.5% formaldehyde-Agarose gel and transferred the output to a Biotran™ nylon membrane (ICN, Montreal, Quebec, Canada) by capillary transfer. [32p]-labeled human $AT_1$-receptor cDNA or hANG cDNA (approximately $1×10^6$ counts/min/ml), which was prepared by using PCR-labelling kit (BRL, Burlington, Ont.), was hybridized with the membrane in a hybridization buffer (50% deionized formamide, 1% sodium dodecyl sulfate (SDS), 0.1% Tween™ 20, 6×SSC [1×SSC, 3 mol/L NaCl, and 0.3 mol/L $Na_3$-citrate, pH 7.0] and 100 µg/ml of denatured salmon sperm DNA) at 42° C overnight. The membrane was washed twice (10 min. each) in 0.1% SDS and 2×SSC at room temperature and then at 50° C ($hAT_1$-receptor probe) or at 65° C. (hANG and β-actin probe). Finally, the membrane was exposed for autoradiography. To standardize the amount of total RNA used, the same blot was hybridized with [$^{32}$P]-labeled cDNA prepared from the hamster β-actin cDNA.

DNA Transfection

Plasmids or fusion genes were transfected into Hep G-2 cells utilizing calcium phosphate endocytosis as described previously (Ming M. et al., *Am. J. Hypertens.*, 1993, 6:141–148). It was previously shown that optimal dose of DNA for gene transfection in mouse hepatoma (Hepa 1–6) cells is 20 μg of supercoiled DNA per 0.5–1×10$^6$ cells (Ming M. et al., *Am. J. Hypertens.*, 1993, 6:141–148). Similar results were obtained in Hep G-2 cells. Thus, in present studies, a total of 20 μg DNA was routinely used in the cell transfection.

To study the effect of AII in the presence or absence of various AII antagonists on the expression of fusion gene in transient gene transfection assays, cells were incubated in DMEM without FBS, 10$^{-9}$ mol/L AII with or without 10$^{-5}$ mol/L AII antagonist were added on day 1 after DNA transfection. The media or cells were harvested on day 2 for assay of IR-hGH or CAT enzymatic activity, respectively.

In order to normalize the efficiency of transfection of pOGH (ANG N-1498/+18), 1 μg of pRSVCAT (a vector with the Rous Sarcoma Virus enhancer/promoter sequence fused to the 5'-end of the CAT coding sequence) was cotransfected with the pOGH (ANG N-1498/+18) (20 μg DNA). The results of pOGH (ANG N-1498/+18) were normalized to the efficiency of transfection of pRSVCAT. The levels of transfection efficiency for pOGH (ANG N-1498/+18) in human hepatoma cells was 25+12% as compared to pRSVCAT.

Hep G-2 Cell Stable Transformants

The method for the selection of stable hepatoma transformants with high expression of pOGH (ANG N-1498/+18) was similar to that described previously for opossum kidney cells (Wang TT et al., *Kidney Int.*, 1994, 46:703–710). Briefly, plasmids pOGH (ANG N-1498/+18) and pRSV-Neo fusion genes were co-transfected (20 μg each) into Hep G-2 cells (1×10$^6$ cells) utilizing calcium phosphate-mediated endocytosis (Ming M. et al., *Am. J. Hypertens.*, 1993, 6:141–148). After transfection, the cells were cultured overnight in 5.0 ml of DMEM containing 10% FBS. Then the medium was replaced with fresh medium containing 10% FBS and 500 μg/ml of aminoglycoside G 418 (Geneticin, Gibco Inc.). The stable transformants which were able to grow in the presence of G 418 and which secreted high levels of IR-hGH into the medium were further subcloned using the method of limiting dilution. Those cells that had passed through at least three repetitions of limiting dilution and continued to secrete high levels of IR-hGH after three months in the presence of G 418 were considered to be stable clones. One clone of human hepatoma (Hep G-TW7) with pOGH (ANG N-1498/+18) integrated into the genomes of Hep G-2 cells was obtained. The clone (Hep G-TW7) was used in accordance with the present invention.

A preferred human liver cell line in accordance with the present invention, which allow to monitor the potency of various AII antagonists on the inhibition of expression of the angiotensinogen-growth hormone (ANG-GH) fusion gene, referred to as Hep G-TW7, has been deposited at the American Type Culture Collection (ATCC, 12301 Parklawn Drive, Rockville, Md. 20852 USA) on Nov. 29, 1994 under deposit number ATCC CRL-11763. This deposit is available to be public upon the grant of a patent to the assignee, Université de Montréal, disclosing same. The deposit is also available as required by Foreign Patent laws in countries wherein counterpart applications are filed.

Figure 1A:
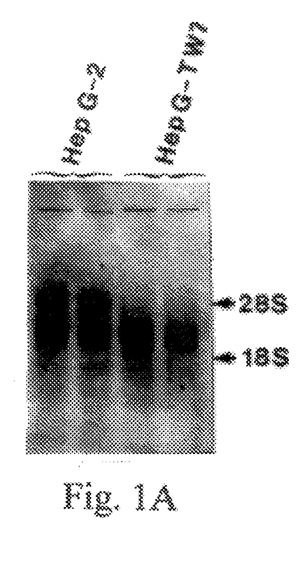
FIG. 1 is a Northern blot analysis of the $AT_1$-receptor mRNA and ANG mRNA in human hepatoma cells.
Figure 1B:
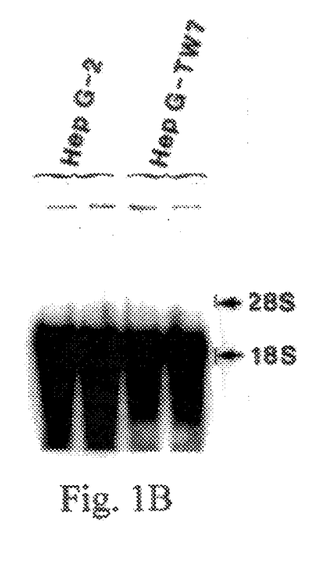
Figure 1C:
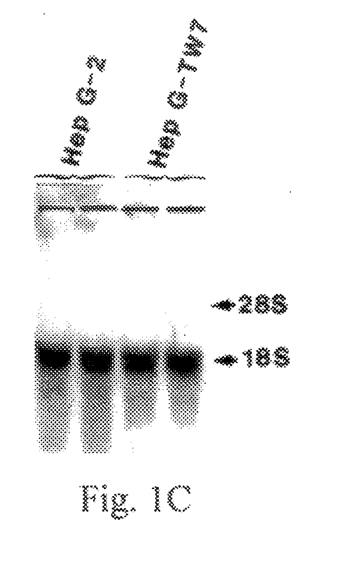

Expression of the Angiotensin II Receptor Messenger RNA (AT$_1$) mRNA and ANG mRNA Total RNA extracted from cultured human hepatoma Hep G-2 and Hep G-TW7 cells was hybridized with labeled human AT$_1$-receptor cDNA and analyzed by Northern blot (FIG. 1A). The same blot was hybridized with hANG cDNA (FIG. 1B) and then with β-actin cDNA probe (FIG. 1C).

Thirty μg of total RNA was separated by Agarose gel electrophoresis and transferred to a nylon membrane. The membrane was hybridized with $^{32}$P-labelled cDNA probes for the human AT$_1$-receptor gene or hANG probe. The same blot was also rehybridized with $^{32}$P-labelled, hamster β-actin cDNA probe to standardize the amount of total RNA used.

The apparent molecular weight of AT$_1$-receptor mRNA and ANG mRNA isolated from human hepatoma cells are both slightly higher than 18S. The AT$_1$-receptor mRNA being higher than ANG mRNA. The presence of AT$_1$-receptor mRNA and ANG mRNA in Hep G-TW7 cells indicate that the expression of these genes have not been suppressed as compared to other transformed cell lines.

Figure 2:
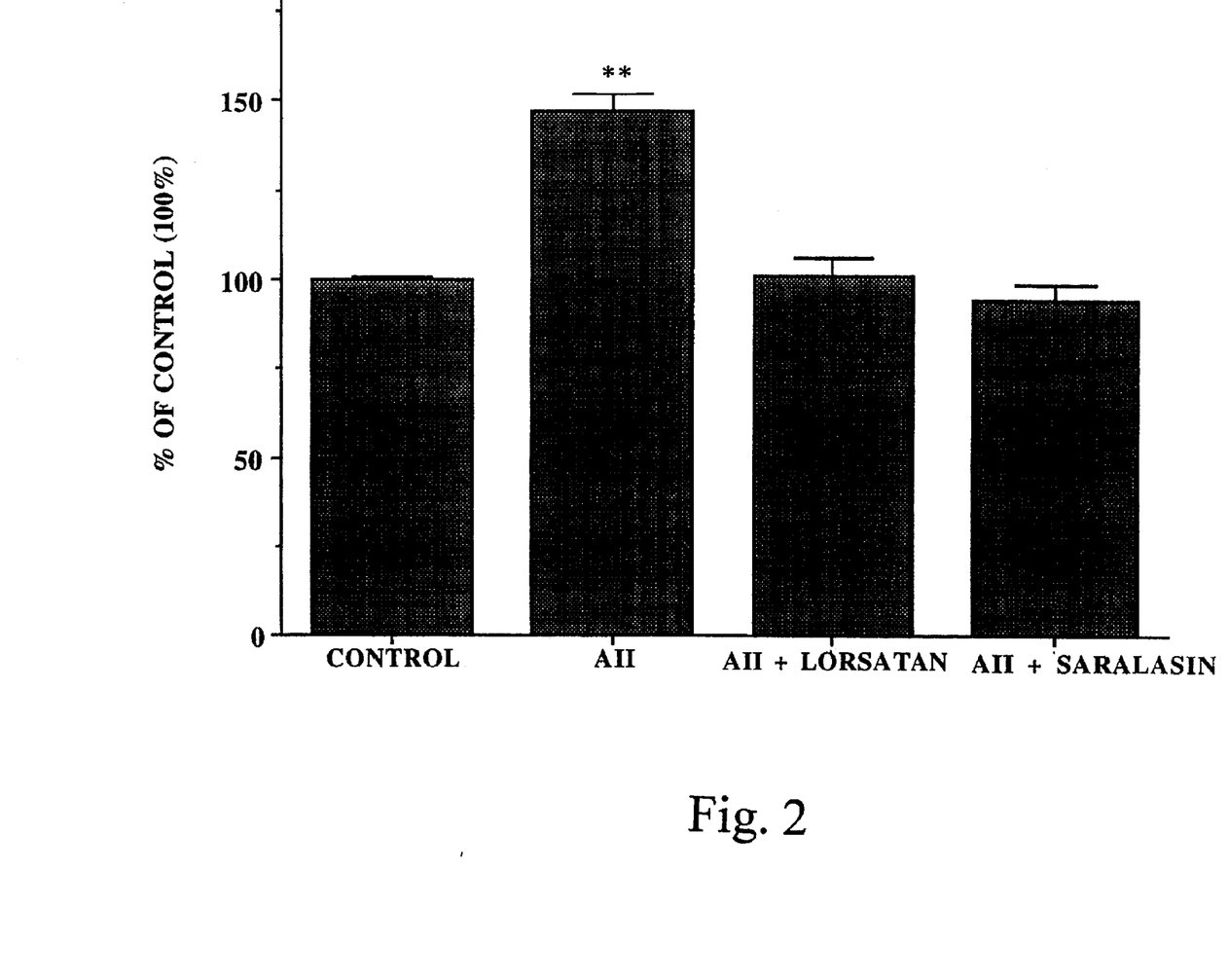
FIG. 2 illustrates the effect of AII on the expression of pOGH (ANG N-1498/+18) fusion gene (transient gene transfection assays) in Hep G-2 cells in the presence of AII-receptor antagonists.

Effect of AII on the Expression of pOGH (ANG N-1498/+18) in Hep G-2 Cells in the Presence or Absence of AII-receptor Antagonist FIG. 2 shows the effect of AII on the expression of pOGH (ANG N-1498/+18) (transient gene transfection assays) in Hep G-2 cells in the presence or absence of Lorsatan™ or Saralasin™. Results are expressed as the percentage of the control (without addition of AII antagonist, 100%), mean ±S.D. AII (10$^{-9}$ mol/L) stimulated the expression of the ANG-GH fusion gene by 1.4-fold (p<0.01) as compared to the control (absence of AII) in Hep G-2 cells. In the presence of Lorsatan™ (10$^{-5}$ mol/L) or Saralasin™ (10$^{-5}$ mol/L), the stimulatory effect of AII was inhibited. CGP 42112A™ (10$^{-5}$ mol/L) had no inhibitory effect.

Basal Expression of pOGH (ANG N-1498/+18) in Hep G-TW7 Cells

Figure 3:
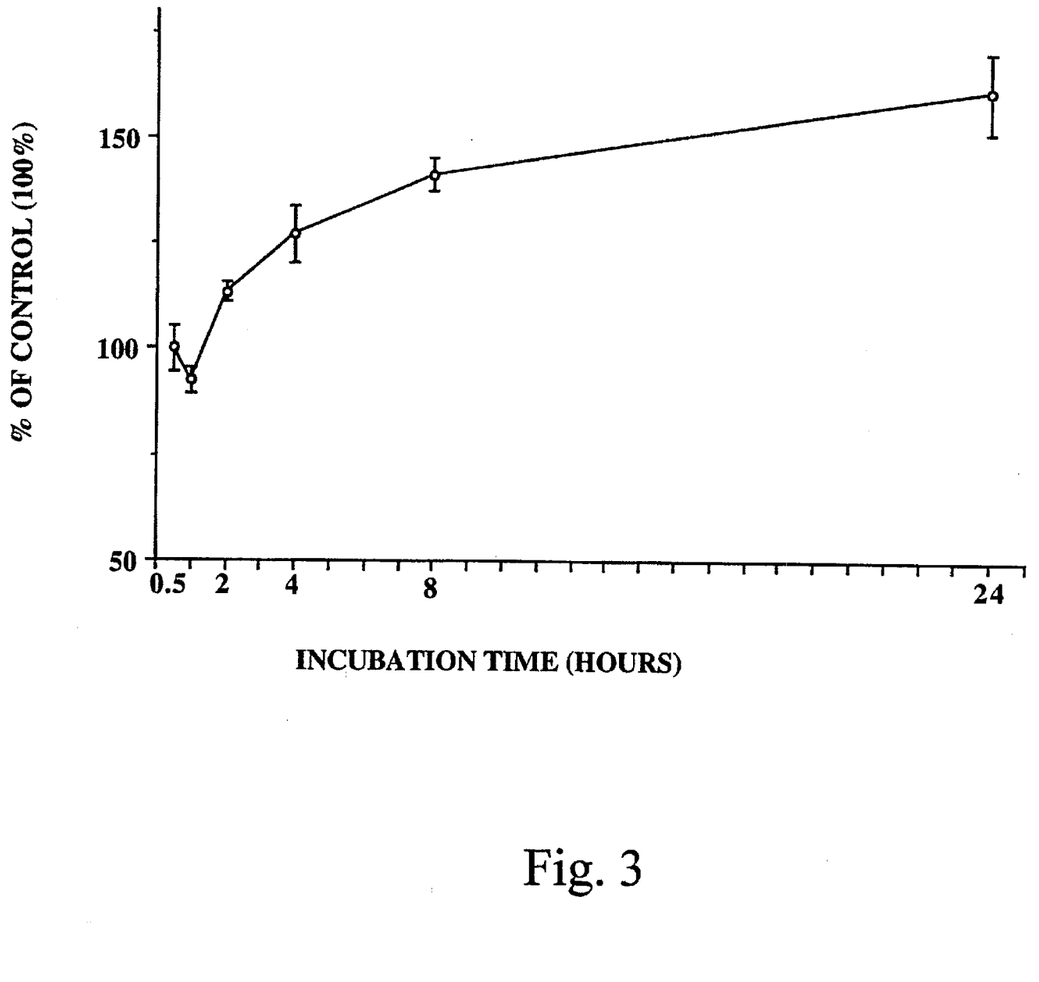
FIG. 3 is the basal expression of the pOGH (ANG N-1498/+18) in Hep G-TW7 cells.

FIG. 3 shows that when Hep G-TW7 cells are plated in 6-well plates and grown in the medium containing 10% FBS up to 48 hours, the amount of IR-hGH detected in the medium were time-dependent. Cells were incubated for 24 hours in DMEM containing 10% fetal bovine serum (FBS). Aliquots (0.5 ml) were taken at different intervals and fresh medium was added to replenish the volume after each aliquot was drawn. The amount of IR-hGH expressed at 30 min. was 4.6±0.9 ng/ml for Hep G-TW7 cells. Each point represents the mean ±S.D. of at least three determinations (*p<0.05, p<0.01 and *p<0.005). The IR-hGH was detectable as early as 30 minutes after incubation and increased with time to reach greater than 1.5-fold in 24 hours as compared to that observed after 30 minutes. In non-transfected Hep G-2 cells, the level of IR-hGH in the medium was less than 0.1 ng/ml.

Effect of AII on the Expression of pOGH (ANG N-1498/+18) in Hep G-TW7 Cells

Hep G-TW7 cells were plated at a density of 1–2×10$^5$ cells/well in 6-well plates and incubated overnight in DMEM containing 1% depleted FBS (dFBS). Then cell growth was arrested by incubation in serum-free medium for 24 hours. Subsequently, various concentrations of AII ($10^{-11}$ to $10^{-5}$ mol/L) were added to the culture medium containing 1% dFBS. At the end of the incubation period, media were collected and kept at $-20°$ C. until assay for IR-hGH.

The depleted FBS was prepared by incubation with 1% activated charcoal and 1% AG 1×8 ion exchange resin (Bio-Rad Laboratories, Richmond, Calif.) for 16 hours or more at room temperature. This procedure removed endogenous steroids and thyroid hormones from the FBS.

Figure 4:
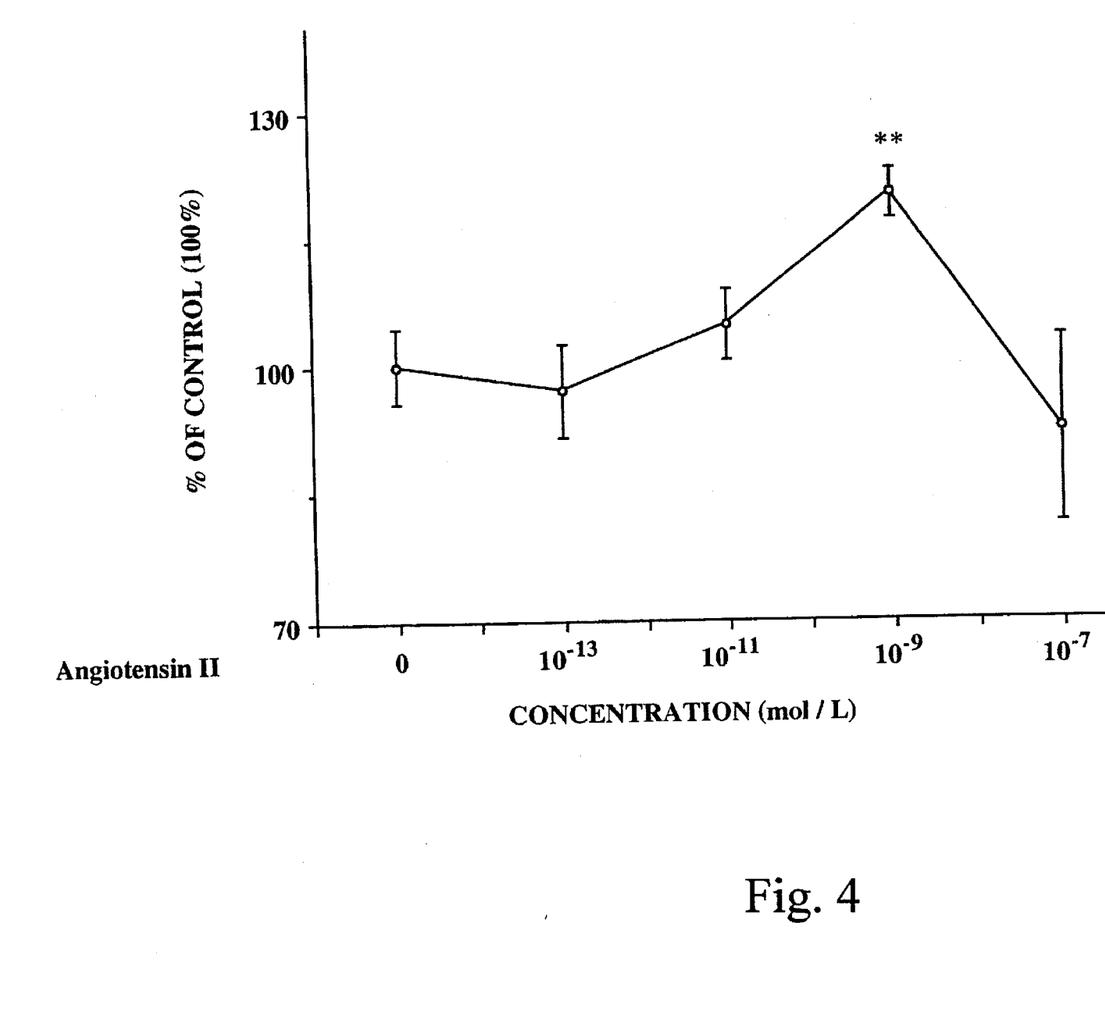
FIG. 4 illustrates the effect of AII on the expression of pOGH (ANG N-1498/+18) in Hep G-TW7 cells.

The effect of AII on the expression of pOGH (ANG N-1498/+18) in HeP G-TW7 cells are shown in FIG. 4. Cells were incubated for up to 24 hours in the presence of various concentrations of AII. Media were harvested after 24 hours of incubation and assayed for IR-hGH. Each point represents the mean ±S.D. of at least three dishes (*$p<0.05$, $p<0.01$ and $p<0.005$). Similar results were obtained from two other experiments. It appears that maximal stimulation of expression of the pOGH (ANG N-1498/+18) was found with $10^{-9}$ mol/L AII ($p<0.01$). At other concentrations of AII, it appears that the stimulatory effect of AII is minimal or inhibited.

Effect of AII on the Expression of POGH (ANG N-1498/+18) in Hep G-TW7 Cells in the Presence of Lorsatan™, Saralasin™ and CGP 42112A™

Hep G-TW7 cells were plated at a density of $1-2\times10^5$ cells/well in a. 6-well plate and incubated overnight in DMEM containing 1% depleted FBS (dFBS). Then cell growth was arrested by incubation in serum-free medium for 24 hours. Subsequently, various concentrations ($10^{-9}$ to $10^{-5}$ mol/L) of Lorsatan™, Saralasin™ and CGP 42112A™ were added to the culture medium containing 1% dFBS in the presence of $10^{-9}$ mol/L AII and incubated for 24 hours. At the end of the incubation period, media were collected and kept at $-20°$ C. until assay.

Figure 5:
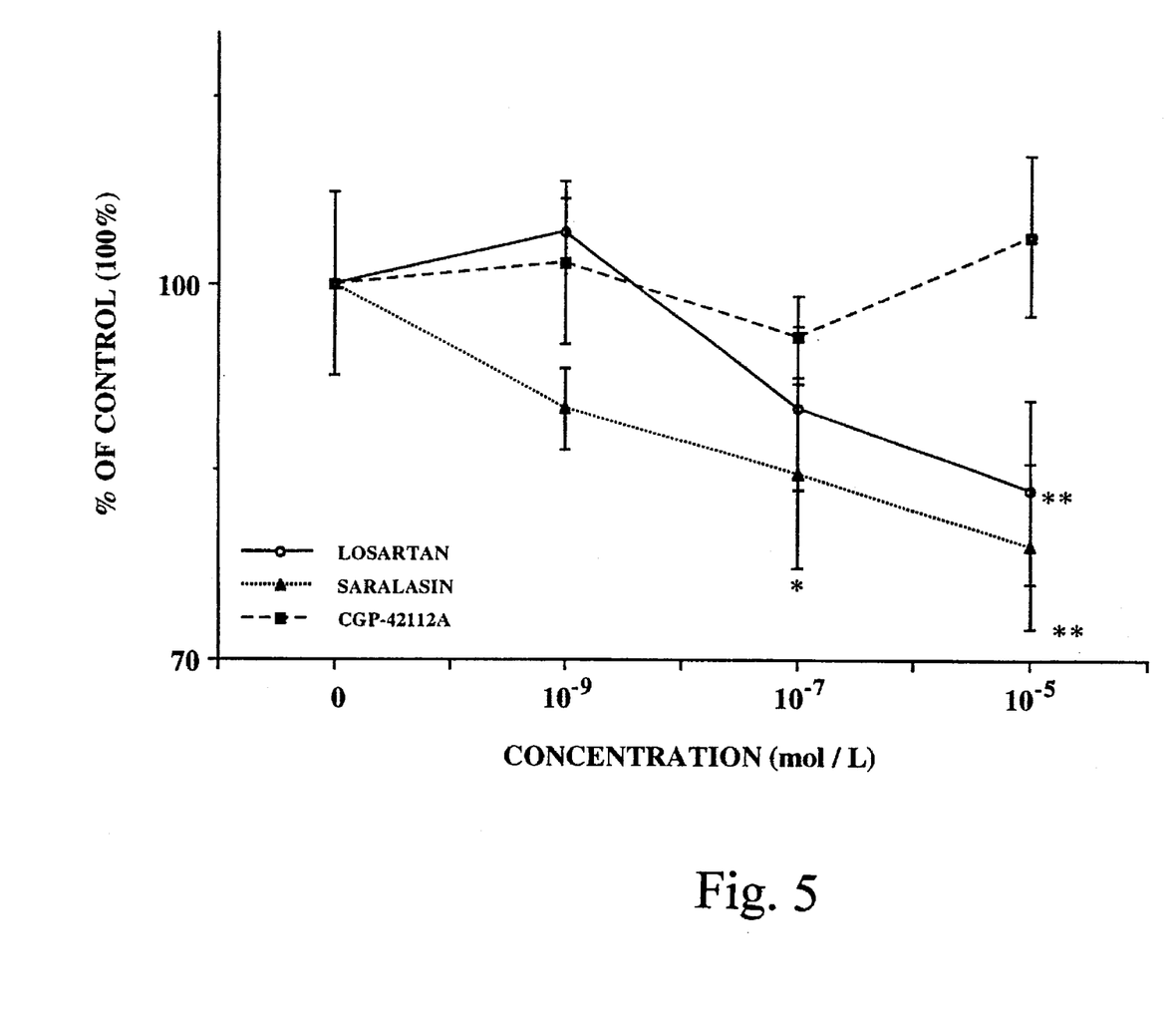
FIG. 5 illustrates the inhibitory effect of AII-receptor antagonists on the expression of pOGH (ANG N-1498/+18) in Hep G-TW7 cells stimulated by AII.

FIG. 5 shows that the addition of either Lorsatan™ ($10^{-9}$ to $10^{-5}$ mol/L) or Saralasin™ ($10^{-9}$ to $10^{-5}$ mol/L) inhibits the stimulatory effect of AII ($10^{-9}$ mol/L) on the expression of pOGH (ANG N-1498/+18) in Hep G-TW7 cells in a dose-dependent manner. Cells were incubated for up to 24 hours in the presence of AII (10–9mol/L) and various concentrations of Lorsatan™ ($10^{-9}$ to $10^{-5}$ mol/L) or Saralasin™ ($10^{-9}$ to $10^{-5}$ mol/L) or CGP 42112A™ ($10^{-9}$ to $10^{-5}$ mol/L). Media harvested and assayed for the level of IR-hGH. Each point represents the mean+S.D. of at least three dishes (*$p<0.05$, $p<0.01$ and *$p<0.005$) (Lorsatan™, Saralasin™, CGP 42112A™). The effective dose for the inhibition of the stimulated expression of the pOGH (ANG N-1498/+18) (by AII) was found with $10^{-9}$ mol/L Lorsatan™ ($P\leq0.01$) and $10^{-7}$ mol/L Saralasin™ ($p<0.05$). CGP 42112A™ was not effective in inhibiting the effect of AII at a concentration as high as $10^{-5}$ mol/L. These studies suggest that the stimulatory effect of AII is mediated via the $AT_1$-receptor(s).

Effect of AII on the Expression of pOGH (ANG N-1498/+18) in Hep G-TW7 cells in the Presence of Staurosporine™

Hep G-TW7 cells were plated at a density of $1-2\times10^5$ cells/well in a 6-well plate and incubated overnight in DMEM containing 1% dFBS. Then cells growth was arrested by incubation in serum-free medium for 24 hours. Subsequently, various concentrations of Staurosporine™ were added to the culture medium containing 1% dFBS in the presence of $10^{-9}$ mol/L AII and incubated for 24 hours. At the end of the incubation period, media were collected and kept at $-20°$ C. until assay.

Figure 6:
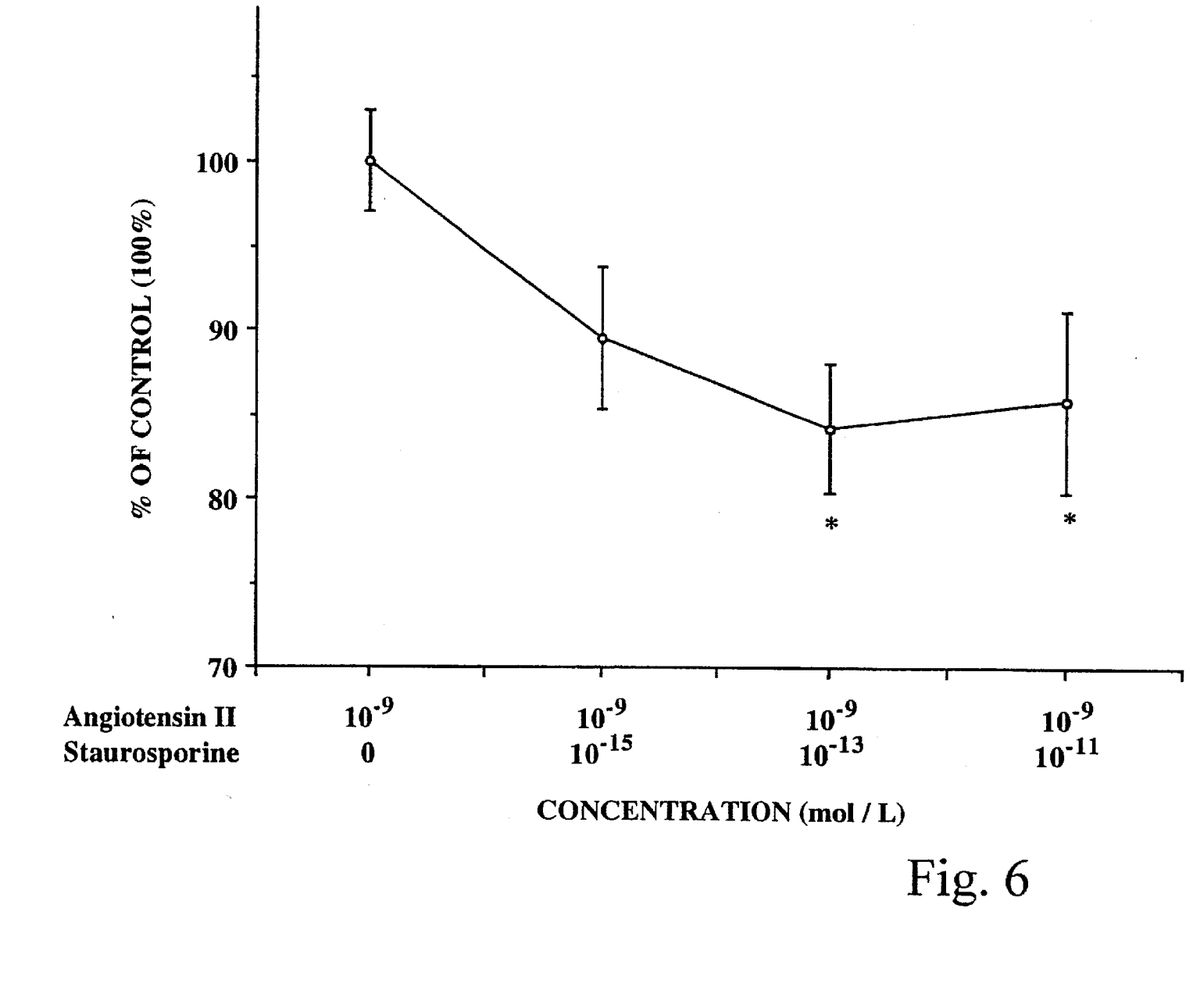
FIG. 6 illustrates the inhibitory effect of Staurosporine™ on the expression of pOGH (ANG N-1498/+18) in Hep G-TW7 cells stimulated by AII.

FIG. 6 shows that the addition of Staurosporine™ inhibits the stimulatory effect of AII on the expression of pOGH (ANG N-1498/+18) in Hep G-TW7 cells in a dose-dependent manner. Cells were incubated for up to 24 hours in the presence of AII ($10^{-9}$ mol/L) and various concentrations of Staurosporine™. Media were harvested and assayed for the level of IR-hGH. Each point represent the mean ±S.D. of at least three dishes (*$p<0.05$, $p<0.01$ and *$P\leq0.005$). The effective inhibition of the stimulated expression of the pOGH (ANG N-1498/+18) was found with $10^{-13}$ mol/L Staurosporine™ ($p<0.05$) in Hep G-TW7 cells. These studies suggest that the protein kinase C is probably involved in the expression of the ANG gene.

Radioimmunoassay (RIA) for hGH

The radioimmunoassay kit for hGH (RIA-hGH) was a gift from NIADDK, NIH, USA. The double antibody RIA procedure was similar to that previously used for the radioimmunoassay of ovine placental lactogen (Chan JSD et al., Endocrinology, 1978, 102:1606–1613). NIAMDD-hGH-1 (AFP-4793 B) was used for both iodination and as a hormone standard.

The limit of sensitivity of the assay was 0.1 ng/ml. The inter- and intra-assay coefficients of variation were 12% (n=10) and 10% (n=10), respectively.

Chloramphenicol Acetyl Transferase (CAT) Assay

The method for the CAT assay has been described previously (Ming M. et al., Am. J. Hypertens., 1993, 6:141–148). The results of all CAT assays are given as a mean+S.D. in triplicates.

Statistical Analysis

The experiments were run three times in triplicate. Values are given as mean+S.D. (n=3) and statistical analysis was done by Student's t test. A probability level of $p<0.05$ was regarded as significant.

DISCUSSION

Within the last several years, AII-receptor ($AT_1$-subtypes) have been identified and cloned by several laboratories (Mauzy CA et al., Biochem. Biophys. Res. Commun., 1992, 186:277–284; Kageyama et al., Biochemistry, 1984, 23:3603–3609). All these studies showed that AII receptor subtypes ($AT_1$-, $AT_2$- and $AT_3$-subtypes) are highly homologous in their coding sequences (greater than 90% homology). Northern blot analysis revealed that the major species of $AT_1$-receptor mRNA in human and bovine tissues is approximately 3.3 Kb, whereas the major species of $AT_1$-receptor mRNA in murine tissues is approximately 2.4 Kb. The data (FIG. 1) by employing a human $AT_1$-receptor cDNA probe and a hANG cDNA probe, showed that the major species of $AT_1$-receptor mRNA and ANG mRNA in human hepatoma cells are 'slightly higher than 18S. Thus, these studies are in agreement with the studies of other investigators.

Numerous studies have demonstrated that AII stimulates the secretion of ANG from the liver both in vitro and in vivo. Studies, employing Northern blot analysis, have also demonstrated that AII stimulates the accumulation of the ANG mRNA in the liver and hepatocytes in vivo and in vitro, respectively. The data presented in FIG. 2, by employing the method of transient gene transfection, showed that the addition of AII ($10^{-9}$ mol/L) stimulates the expression of pOGH (ANG N-1498/+18) by 1.4-fold ($p<0.01$) as compared to the controls (absence of AII) in Hep G-2 cells. In the presence of Lorsatan™ or Saralasin™, the stimulatory effect of AII was blocked. The addition of CGP 42112A™ had no effect. The results supported that AII has a stimulatory effect on the expression of the ANG gene in the liver in vitro. Furthermore, the stimulatory effect of AII is mediated via the $AT_1$-receptor, and not the $AT_2$-receptors.

In accordance with the present invention, the plasmid pOGH (ANG N-1498/+18) was employed to study the effect of AII (FIGS. 2 to 6). Since receptors for hGH are presented in Hep G-2 cells, this raised the possibility that the hGH secreted into the medium may have a stimulatory effect on the expression of the ANG gene. Thus, in order to investigate this possibility, transient gene transfection experiments were performed by employing pOCAT (ANG N-1498/+18) (Ming M. et al., *Am. J. Hypertens.*, 1993, 6:141–148), in the presence of hGH. No significant increase of expression of pOCAT (ANG N-1498/+18) by the addition of hGH as high as 4.5 mmol/L was observed. Thus, it was concluded that hGH has no stimulatory effect on the expression of ANG gene in hepatoma cells. The use of plasmid pOGH (ANG N-1498/+18) in accordance with the present invention is appropriate.

Clone Hep G-TW7 is a stable transformant with pOGH (ANG N-1498/+18) integrated into Hep G-2 cellular genome. This clone has been grown in a medium containing 500 µg/ml of G418 for more than three months and secreted a high amount of IR-hGH into the medium. The expression of pOGH (ANG N-1498+18) in Hep-TW7 cells was time-dependent (FIG. 3) with greater than 1.5 to 2-fold in 24 hours, as compared to that observed after 30 minutes. These results indicated that the IR-hGH is not retained within the cells.

The present invention showed that AII stimulates the expression of pOGH (ANG N1498/+18) in Hep G-TW7 cells (FIG. 4A) with an effective does at $10^{-9}$ mol/L. At present, it is not know why high concentrations of AII (i.e greater than $10^{-9}$ mol/L) had minimal or no stimulatory effect on the expression of pOGH (ANG N-1498/+18). One possible explanation may be that the exposure of cells to high levels of AII might desensitize the AII receptors. This possibility is supported by the studies on β-adrenoreceptors, that exposure of cells to high levels of agonist rapidly desensitizes the β-adrenoreceptors. Nevertheless, more studies are warranted to confirm this possibility in Hep G-2 cells.

The addition of either Lorsatan™ ($10^{-9}$ to $10^{-5}$ mol/L) or Saralasin™ ($10^{-9}$ to $10^{-5}$ mol/L) inhibits the stimulatory effect of AII ($10^{-9}$ mol/L) on the expression of pOGH (ANG N-1498/+18) in Hep G-TW7 cells (FIG. 5), whereas CGP 42112A™ had no effect. These studies confirmed the transient gene transfection assays in accordance with the present invention (FIG. 2) and further supported that the effect is mediated via $AT_1$-receptors and not $AT_2$-receptors. Most interestingly, it was observed that the addition of Staurosporine™ (an inhibitor of PKC) inhibits the stimulatory effect of AII on the expression of pOGH (ANG N-1498/+18) in Hep G-TW7 cells (FIG. 6). These studies indicated that the effect of AII is probably mediated via the PKC pathway. Definitely, more experiments are necessary to elicidate the molecular mechanism(s) of AII on the expression of the ANG gene via the PKC pathway.

In summary, the studies of the present invention showed that the addition of AII stimulates the expression of the ANG-GH fusion gene. $AT_1$-receptor(s) and PKC are probably involved in the signal transduction pathway of AII. The studies of the present invention raise the possibility that AII may exert dual effects on the expression of the ANG gene in the liver. First, AII inhibits adenylyl cyclase system and stabilizes the ANG mRNA. Secondly, AII may stimulate the PKC system and subsequently enhance the expression of the ANG gene.

Finally, Hep G-TW7 cells with pOGH (ANG N-1498/+18) integrated into their genome provide an excellent in vitro model system to study the regulation of the expression of the ANG gene.

The present invention will be more readily understood by referring to the following example which is given to illustrate the invention rather than to limit its scope.

EXAMPLE I

In vitro Test for the Evaluation of Angiotensin II Antagonists on Angiotensinogen Expression Methods Hep G-TW7 cells were plated at a density of $1-2\times10^5$ cells/well in 6-well plates and incubated overnight in DMEM containing 1% depleted fetal bovine serum (dFBS). Then cell growth was arrested by incubation in serum-free medium for 24 hours. Subsequently, various concentrations ($10^{-11}$ to $10^{-5}$ mol/L) of angiotensin I (AI) or angiotensin III (AIII) were added to the culture medium containing 1% dFBS. At the end of the 24 hours incubation period, media were collected and kept at −20° C. until assay for IR-hGH.

Results

Figure 7:
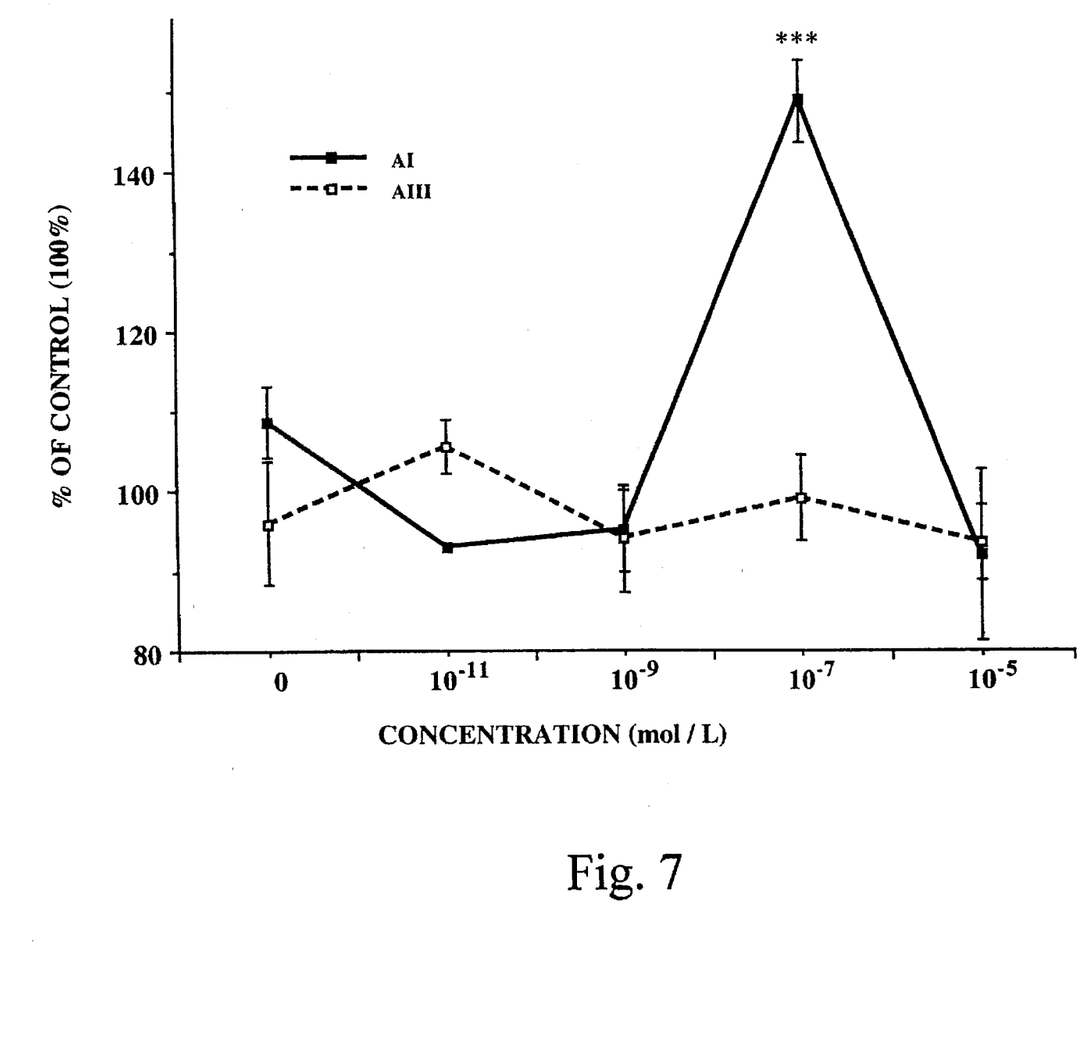
FIG. 7 illustrates the inhibitory effect of angiotensin I (AI) and angiotensin III (AIII) on the expression of pOGH (ANG N-1498/+18) in Hep G-TW7 cells.

The effects of AI and AIII on the expression of pOGH (ANG N-1498/+18) in Hep G-TW7 cells are shown in FIG. 7. It appears that maximal stimulation of expression of the pOGH (ANG N-1498/+18) was found with $10^{-7}$ mol/L AI ($p \leq 0.005$). At concentration greater or lesser than $10^{-7}$ mol/L, it appears that the stimulatory effect AI is minimal. On the other hand, AIII was not effective in stimulating the expression of pOGH (ANG N-1498/+18) in Hep G-TW7 at dose as high as $10^{-5}$ mol/L.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

I claim:

1. A transformed human liver cell line which is stably transfected with at least one DNA construct coding for at least a 5'-flanking region of an angiotensinogen (ANG) gene operatively linked upstream to a human growth hormone gene, thereby forming an angiotensinogen-human growth hormone fusion gene, and which transformed human liver cell line expresses said angiotensin-human growth hormone fusion gene.

2. The transformed human liver cell line of claim 1, wherein said DNA construct is a pOGH fusion gene.

3. The transformed human liver cell line of claim 1, wherein said DNA construct is pOGH and which is ATCC deposit number CRL-11763.

4. An in vitro test for the evaluation of the efficacy of one or more angiotensin II (AII) antagonist on the inhibition of expression of angiotensinogen (ANG) gene in vivo, which comprises administering one or more AII antagonist to the transformed human liver cell line of claim 1 and monitoring the expression of human angiotensinogen-growth hormone to evaluate the efficacy of said one or more AII antagonist to inhibit ANG expression.

5. The in vitro test of claim 4, wherein administering of said one or more AII antagonist is effected using a concentration of about $10^{-9}$ mol/L to about $10^{-5}$ mol/L of antagonist.

6. The in vitro test of claim 4, wherein said monitoring is effected using radioimmunoassay based on immunoreactive human growth hormone (IR-hGH).

\* \* \* \* \*